US00PP08249P

United States Patent [19]

Jessel, Jr.

[11] Patent Number: Plant 8,249

[45] Date of Patent: Jun. 8, 1993

[54] CARNATION PLANT NAMED CFPC SERENITY

[75] Inventor: Walter H. Jessel, Jr., Salinas, Calif.

[73] Assignee: California Florida Plant Co., L.P., Salinas, Calif.

[21] Appl. No.: 757,839

[22] Filed: Sep. 11, 1991

[51] Int. Cl.[5] ..... A01H 5/00

[52] U.S. Cl. ..... Plt./70.5

[58] Field of Search ..... Plt./70.2, 70.5, 70.6, Plt./71.1, 72.1

*Primary Examiner*—Howard J. Locker

*Attorney, Agent, or Firm*—Christie, Parker & Hale

[57] ABSTRACT

A new carnation of pink coloration.

1 Drawing Sheet

SUMMARY OF THE INVENTION

The present invention relates to a new and distinct variety of carnation plant which was originated by me in a controlled breeding program by my crossing as seed parent, the variety known as 'Pamela' (varietal denomination 'Lontrelos') (U.S. Plant Pat. No. 5,580) and as pollen parent, the variety known as 'Babella' (varietal denomination 'Lonkorpi') U.S. Plant Pat. No. 5,433). The varietal denomination of this new carnation is 'CFPC Serenity'.

Among the novel combination of characteristics possessed by the new variety which distinguishes it are its attractive pink flowers that resist fading, and ability to produce cuttings that are easy to root. Flowers of the new variety are produced as spray-type blooms suitable for cut flower production.

'CFPC Serenity' differs in flower color from its pollen parent, 'Babella' which produces yellow picotee crimson flowers, and from its seed parent, 'Pamela', in resistance to color fading, since 'Pamela' fades badly. The new variety also differs in bud count per plant since 'Pamela' "singles out" to one and two buds per stem and the new variety retains a higher bud count per stem during low light periods. Cuttings of 'CFPC Serenity' are easier to root, e.g. 12 to 14 days, than 'Pamela' which roots in 18 to 20 days with a high loss percentage. The new variety also flowers 2 to 3 weeks earlier than 'Pamela' from the same planting date.

Asexual reproduction by propagation by side shoot cuttings of the new variety as performed in Fremont and Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Serenity'.

BRIEF DESCRIPTION OF THE ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (RHSCC). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont and Salinas, Calif. The height of plant and flower and foliage size are established as an average using standard commercial cultural practices.

Name: CFPC Serenity.

Classification:

*Botanical.*—Hybrid *Dianthus caryophyllus.*

*Commercial.*—Carnation, spray type.

Parentage:

*Female parent.*—'Pamela'.

*Male parent.*—'Babella'.

PLANT

Height: About 35 inches.

Growing habit: Herbaceous, semi-upright.

Blooming habit: Terminal as a spray.

Blooming season: Year round.

Rooting time: About 12–14 days.

Mutation prone: Does not appear to be.

Disease resistance: Unknown.

Temperature tolerance: Wide range for carnation.

Breaking action: Good.

Foliage:

*Color.*—Upper side: Near to 131A. Lower side: Near to 133A.

*Size.*—About 5½ inches long, about ½ to ¾ inch wide, at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Ovoid.

*Color.*—Near to 143A.

*Length.*—About 1-inch.

*Diameter.*—About ⅔-inch.

Calyx:

*Number of lobes (sepals).*—About 6.

*Length.*—About ⅞ to 1-inch.

*Width.*—About ⅔-inch.

*Color.*—Outside — near to 143A. Inside — near to 138D.

Bloom:

*Shape.*—Round.

*Size.*—Diameter average: About 2¼ inches. Depth average: About 1 inch.

*Borne.*—Terminal as a spray.

*Color.*—General tonality: Light salmon pink. Upper side: Near to from 56A to 56B. Lower side: Near to 56D. Center: Near to 56A. Outer petals: Near to from 56A to 56B.

*Keeping quality.*—10-12 days.

*Fragrance.*—Slight.

*Permanenace.*—Dry up on receptacle.

Petals:

*Number.*—About 37.

*Outer petals.*—Length: About 1½ inches. Width: About ¾-inch.

*Central petals.*—Length: About 1-inch. Width: About ⅝-inch.

*Texture.*—Smooth.

*Form.*—Fan shaped.

*Appearance.*—Shiny.

REPRODUCTIVE ORGANS

Not visible in this variety.

Stamens:

*Number.*—About 10 to 11.

*Arrangement.*—Around the ovary.

Anthers:

*Length.*—About ⅛ to ¼ inch.

*Color.*—Near to 159A.

Filaments:

*Length.*—About 170 to ¾-inch.

*Color.*—Near to 158C.

Pistil:

*Number.*—About 3.

*Color.*—Style — near to 155A.

Stigma:

*Number.*—About 3.

*Color.*—Near to 155B to white.

Ovary:

*Shape.*—Conical, ribbed.

*Color.*—Base — greenish white. Body — greenish yellow. Apex — tan.

I claim:

1. A new and distinct variety of carnation plant, substantially as shown and described.

* * * * *

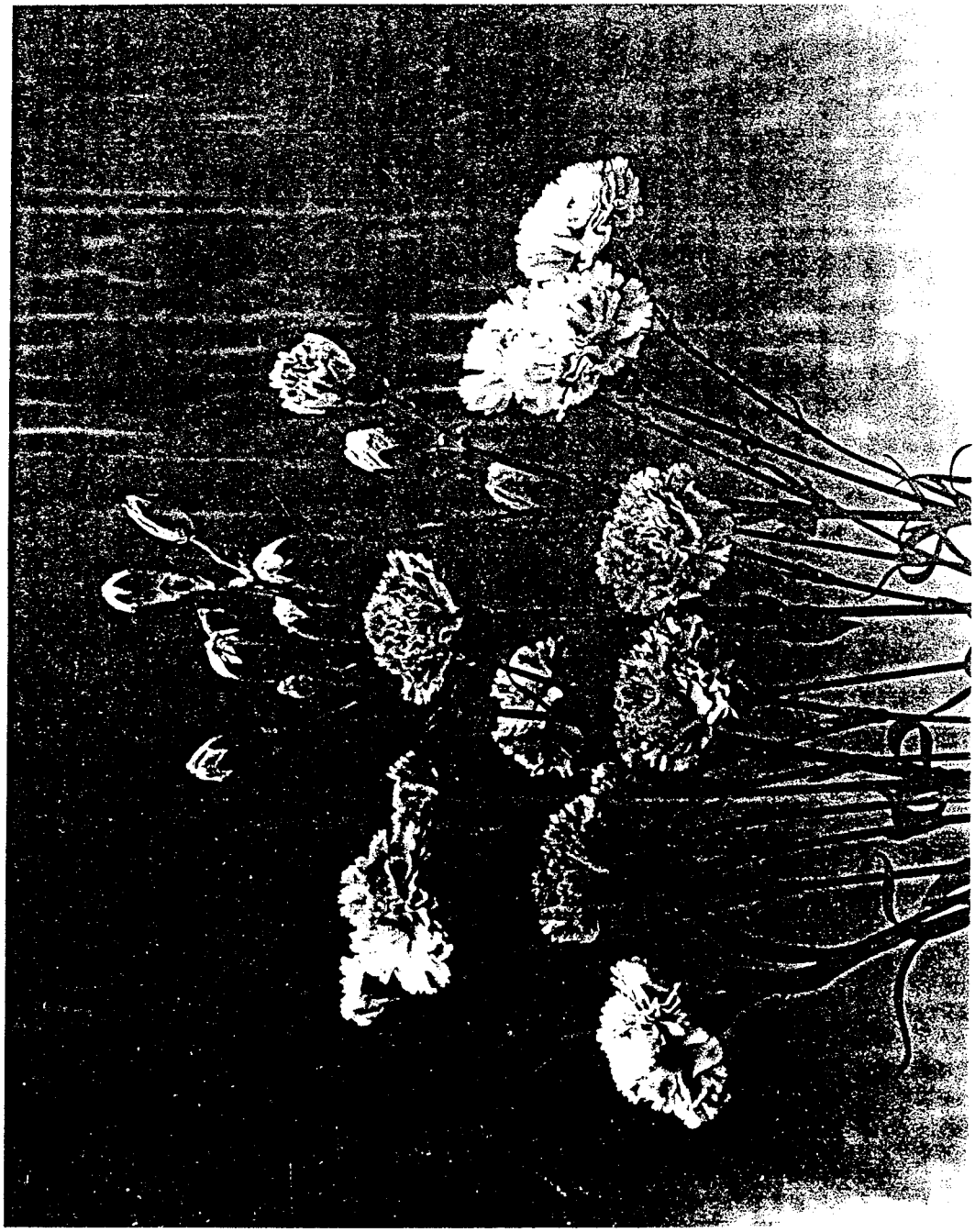

UNITED STATES PATENT AND TRADEMARK OFFICE

CERTIFICATE OF CORRECTION

PATENT NO. : Plant 8,249

DATED : June 8, 1993

INVENTOR(S) : Walter H. Jessel, Jr.

It is certified that error appears in the above-indentified patent and that said Letters Patent is hereby corrected as shown below:

Column 3, line 12, change "Permanenace" to -- Permanence --.

Column 4, line 8, change "170" to -- 2/3 --.

Signed and Sealed this

Twenty-first Day of June, 1994

*Attest:*

Bruce Lehman

BRUCE LEHMAN

*Attesting Officer*

*Commissioner of Patents and Trademarks*